US009649131B2

(12) United States Patent
Beijens et al.

(10) Patent No.: US 9,649,131 B2
(45) Date of Patent: May 16, 2017

(54) MICRODERMABRASION DEVICE (71) Applicant: KONINKLIJKE PHILIPS N.V., Eindhoven (NL)

(72) Inventors: Linda Goverdina Maria Beijens, Eindhoven (NL); Martin Jurna, Eindhoven (NL); Antonius Maarten Nuijs, Eindhoven (NL); Maria Angelina Josepha Grootel-Rensen, Eindhoven (NL); Caecilia Hendrina Theodora Chlon, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/767,309

(22) PCT Filed: Feb. 24, 2014

(86) PCT No.: PCT/IB2014/059196
§ 371 (c)(1),
(2) Date: Aug. 12, 2015

(87) PCT Pub. No.: WO2014/136013
PCT Pub. Date: Sep. 12, 2014

(65) Prior Publication Data
US 2016/0008031 A1    Jan. 14, 2016

(30) Foreign Application Priority Data
Mar. 4, 2013    (EP) ..................................... 13157601

(51) Int. Cl.
*A61B 17/54*    (2006.01)
*A61B 90/00*    (2016.01)

(52) U.S. Cl.
CPC ............ *A61B 17/54* (2013.01); *A61B 17/545* (2013.01); *A61B 90/06* (2016.02);
(Continued)

(58) Field of Classification Search
CPC . A61B 17/54; A61B 17/545; A61B 2090/062; A61B 2090/0807; A61B 2090/0818; A61B 2217/005; A61B 90/06
See application file for complete search history.

(56) References Cited

U.S. PATENT DOCUMENTS 6,241,739 B1    6/2001    Waldron
6,726,693 B2    4/2004    Weber
(Continued)

FOREIGN PATENT DOCUMENTS

DE    102009016550 A1    10/2010
KR    20050013421 A    2/2005
(Continued)

*Primary Examiner* — Julie A Szpira (57) ABSTRACT

The present application relates to a microdermabrasion device (1). The device has a suction path (11) along which skin fragments removed by the device are drawn, and a detection unit (3) configured to determine one or more characteristics of skin fragments drawn along the suction path. The detection unit is configured to determine the depth of abrasion performed by the device based on the one or more characteristics of skin fragments drawn along the suction path. The present application also relates to a method of determining the operating depth of abrasion of a microdermabrasion device.

15 Claims, 2 Drawing Sheets

(52) U.S. Cl.
CPC . *A61B 2090/062* (2016.02); *A61B 2090/0807* (2016.02); *A61B 2090/0818* (2016.02); *A61B 2217/005* (2013.01)

(56) References Cited

U.S. PATENT DOCUMENTS

| | | | |
|---|---|---|---|
| 8,226,663 B2 | 7/2012 | Remsburg | |
| 2006/0100567 A1* | 5/2006 | Marchitto | A61B 17/54 604/19 |
| 2008/0249537 A1* | 10/2008 | Chung | A61B 17/54 606/131 |

FOREIGN PATENT DOCUMENTS

| | | | |
|---|---|---|---|
| KR | 20070053883 A | 5/2007 |
| WO | 9512357 A1 | 5/1995 |
| WO | 2008134545 A1 | 11/2008 |

* cited by examiner

MICRODERMABRASION DEVICE

This application is the U.S. National Phase application under 35 U.S.C. §371 of International Application No. PCT/IB2014/059196, filed on Feb. 24, 2014, which claims the benefit of European Application No. 13157601.9 filed on Mar. 3, 2013. These applications are hereby incorporated by reference herein.

FIELD OF THE INVENTION

The present application relates to a microdermabrasion device. The present application also relates to a method of determining the operating depth of abrasion of a microdermabrasion device.

BACKGROUND OF THE INVENTION

It is known to provide exfoliation of skin as a light cosmetic procedure. Such a procedure is used to remove dead cells from the outermost layer or layers of the skin. This provides a means of rejuvenating the skin, clearing pores and minimising lines and other marks found on the surface of skin.

One such procedure used to remove dead cells from the outermost layer or layers of the skin is microdermabrasion. Microdermabrasion uses a mechanical medium for exfoliation to remove dead skin cells from the outermost layer or layers of skin, referred to as the epidermis. Benefits include epidermal thickening and collagen deposition.

Microdermabrasion devices generally comprise two parts: an abrasive material to act on and remove the outermost layer or layers of skin, and a suction means to gently lift up the skin and draw the discarded skin particles away from the operating area.

Microdermabrasion devices work by either particle abrasion or non-particle abrasion. With particle abrasion a high pressure stream of particles, such as aluminium oxide, magnesium oxide, sodium chloride, or sodium bicarbonate particles are directed towards the skin to abrade the skin and remove skin fragments from the upper layer or layers of skin. A vacuum is also produced to remove the abrasive particles and exfoliated skin fragments from the area of the skin. With non-particle abrasion, a roughened surface, such as a diamond grit-embedded surface, is moved over the skin to abrade the skin and remove skin fragments from the upper layer or layers of skin.

The skin has two primary layers—the epidermis and the dermis. The epidermis comprises the outermost layers of the skin. Such layers include the stratum corneum (the outermost layer), the stratum lucidum, stratum granulosum, stratum spinosum, and stratum basale. It has been found that removal of the stratum corneum at least aids the beneficial results of microdermabrasion. Therefore, it is necessary to ensure that a suitable depth of abrasion is applied to the skin. However, it has also been found that if the depth of abrasion exceeds a certain level then irritation of the skin or bleeding may occur.

It is known to attempt to achieve a desired depth of abrasion of the skin by applying a predetermined number of passes of the microdermabrasion device to the skin. However, such a method is inaccurate and does not take into account other variables such as different skin types, location of the skin and condition of the skin.

It is to be noted that US patent application US 2008/0249537 A1 discloses a skin treatment device having an abrasive tip comprising a suction hole through which loosened skin particles are removed. The skin treatment device further comprises a sensor to measure the oiliness of the skin to be treated which measurement is used to control the suction. The skin sensor is disclosed to be separate from the treatment unit and to measure the oiliness of untreated skin.

It is further to be noted that international patent application WO 95/12357 A1 discloses a device for removing the stratum corneum by repeatedly placing an adhesive film on a defined area of the skin. The device according to WO 95/12357 A1 comprises a light source to shine a beam of light onto a used part of the adhesive film in order to allow visual inspection of the attached stratum corneum.

It is further to be noted that WO 2008/13454 A1 discloses a device for increasing the skin's permeability by abrasing the skin. The device of WO 2008/13454 A1 comprises a feedback control mechanism based on two electrodes measuring the conductance of the remaining skin which conductance is supposed to be a measure for skin permeability.

Finally, it is to be noted that US 2006/100567 A1 discloses a device for altering tissue by means of an applicator comprising control means to monitor a physical property of the remaining skin.

SUMMARY OF THE INVENTION

It is an object of the invention to provide a microdermabrasion device and/or a method of determining the operating depth of abrasion of a microdermabrasion device which substantially alleviates or overcomes the problems mentioned above, amongst others.

According to the present invention, there is provided a microdermabrasion device comprising a suction path along which skin fragments removed by the device are drawn, and a detection unit configured to determine one or more characteristics of skin fragments drawn along the suction path, wherein the detection unit is configured to determine the depth of abrasion performed by the device based on the one or more characteristics of skin fragments drawn along the suction path.

With this arrangement it is possible to actively determine the depth of abrasion performed on the skin of a user. Therefore, it is possible to ensure that the user achieves a desired depth of abrasion, and/or prevent the removal of an excess number of layers of skin. This prevents damage and/or restricts irritation to a user's skin due to use of the microdermabrasion device.

The detection unit may further comprise a detector disposed on the suction path to detect one or more characteristics of skin fragments drawn along the suction path.

Therefore, the detection unit is able to easily determine one or more of the characteristics of skin fragments abraded from a user's skin passing along the suction path. The above arrangement also provides a simple means of sensing one or more characteristics of the skin fragments.

The detector may be a first detector and the detection unit may further comprise a second detector disposed on the suction path to detect skin fragments drawn along the suction path.

By providing a second detector, it is possible to maximise the accuracy of the detection unit. It also provides redundancy in case of failure of one of the detectors, or if one of the detectors is obscured.

The first and second detectors may be configured to detect different characteristics of skin fragments drawn along the suction path.

With this arrangement, the detection unit is able to more easily determine the depth of abrasion taking into account variances between differences in skin.

The detector may comprise a photosensor.

The detection unit may further comprise a feedback module configured to provide feedback to the user based on the operating depth of abrasion determined by the detection unit.

Therefore, it is possible for a user to easily determine the correct depth of abrasion.

The detection unit may be configured to determine the number of skin fragments drawn along the suction path.

With the above arrangement it is possible to easily detect and determine a variable characteristic of the skin fragments. The number of skin fragments removed from a skin part may provide feedback on the depth of the treatment, in which the depth of abrasion correlates to the efficacy and potential side effects.

The detection unit may be configured to determine the size of skin fragments drawn along the suction path.

This means that it is relatively straightforward to provide a detection unit capable of determining a characteristic of the skin fragments, for example a simple light source and light detector.

The detection unit may be configured to determine the temperature of skin fragments drawn along the suction path.

With this arrangement it is possible to maximise the accuracy of the determined abraded depth.

The detection unit may be configured to determine the weight of skin fragments drawn along the suction path.

With this arrangement it is possible to determine additional attributes of the skin fragments, such as the molecular composition of the skin fragments.

The detection unit may be configured to determine the water content of skin fragments drawn along the suction path.

Therefore, it is also possible to provide alternative feedback, such as skin hydration and/or skin barrier quality.

The detection unit may be configured to determine the scattering co-efficient of skin fragments drawn along the suction path. By determining the scattering co-efficient it is possible to obtain an indication of the skin hydration in the different skin layers. The detection unit may be configured to determine the absorption profile of skin fragments drawn along the suction path, or the absorption of a single wavelength of skin fragments drawn along the suction path.

Therefore, it is possible to identify the type of skin fragments/cells that are abraded. By measuring the absorption profile of skin fragments it is also possible to provide feedback about skin type and efficiency of treatments. This may also help to adapt the treatment protocol towards an individualized treatment profile.

The feedback module may be configured to provide a visual, mechanical and/or audible indication.

The microdermabrasion device may be a non-particle microdermabrasion device.

With such an arrangement it is relatively straightforward to determine skin particles passing through the detection unit.

According to another aspect of the invention, there is provided a method of determining the depth of abrasion of a microdermabrasion device, comprising determining one or more characteristics of skin fragments drawn along a suction path of the device, and determining the depth of abrasion performed by the device based on the one or more characteristics of skin fragments drawn along the suction path.

The method may further comprise determining one or more of the volume of skin fragments drawn along the suction path, the size of skin fragments drawn along the suction path, the temperature of skin fragments drawn along the suction path, the weight of skin fragments drawn along the suction path, the water content of skin fragments drawn along the suction path, the scattering co-efficient of skin fragments drawn along the suction path, the absorption profile of skin fragments drawn along the suction path, and/or the absorption or a single wavelength of the skin fragments drawn along the suction path.

The method may further comprise providing visual or audible feedback based on the determined depth of abrasion.

The method of determining the depth of abrasion of a microdermabrasion device may be a method of determining the depth of abrasion of a non-particle microdermabrasion device.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
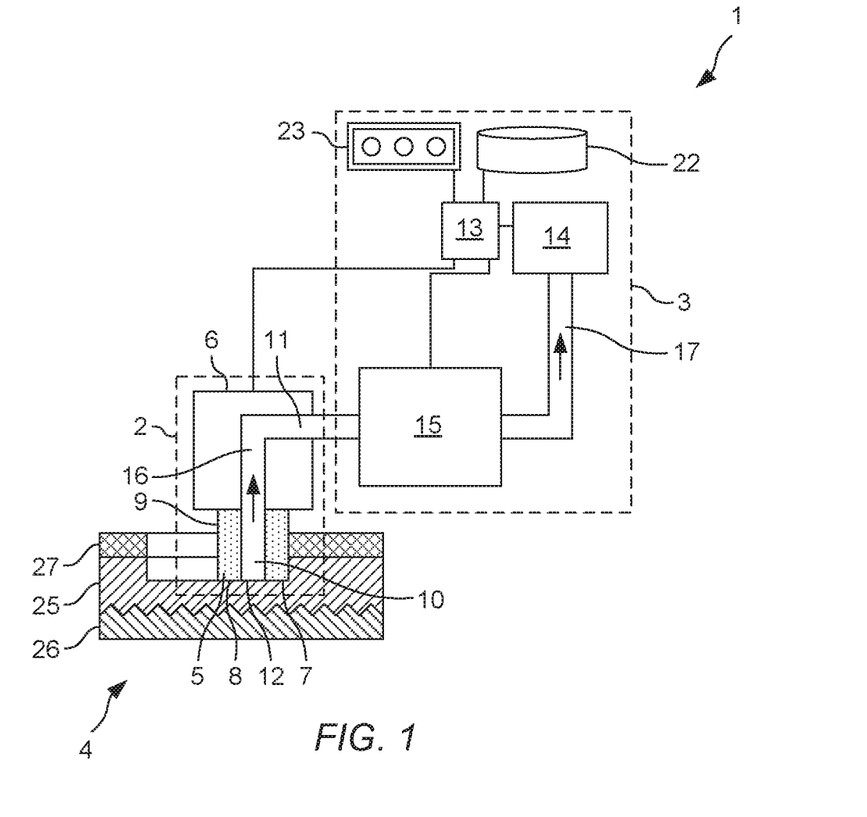
FIG. 1 shows a schematic diagram of a microdermabrasion device.

FIG. 1 shows a schematic diagram of a microdermabrasion device 1. The microdermabrasion device 1 is a non-particle microdermabrasion device. The non-particle microdermabrasion device has a head unit 2 and a detection unit 3. The head unit 2 is configured to act on a user's skin 4 to abrade the outer layer or layers of the skin and remove skin fragments (not shown) from the outer layer or layers of skin 4. The detection unit 3 is configured to determine characteristics of the skin fragments, as will be explained hereinafter. The detection unit 3 is also configured to draw abraded skin fragments away from the skin 4.

The microdermabrasion device 1 is configured to act on the skin to produce a depth of abrasion of the skin 4. That is, the layer or part of a layer that the skin exposes due to the removal of the outer layers and/or part of a layer.

The head unit 2 comprises an abrasive head 5 and a drive unit 6. The abrasive head 5 has an abrasive surface 7. The abrasive surface 7 is formed on an outer surface of the abrasive head 5. In the present arrangement, the abrasive head 5 is generally cylindrical with a base surface 8 and a side surface 9. The abrasive surface 7 is formed on the base and side surfaces 8, 9. It will also be understood that alternative arrangements are envisaged.

The abrasive surface 7 is formed by diamond grit bonded on the outer surface of the abrasive head 5 using a bonding agent. It will also be understood that alternative abrasive surfaces are envisaged.

A bore 10 is formed through the head unit 2. The bore 10 forms part of a suction path 11 along which skin fragments removed from the skin 4 are drawn, as will be explained below. An inlet 12 to the suction path 11 is defined in the abrasive head 5. The inlet 12 is formed in the abrasive surface 7, although it will be understood that one or more alternative apertures may be formed in the abrasive head 5 to form the inlet 12.

The drive unit 6 is configured to rotate the abrasive head 5 about its longitudinal axis. The drive unit 6 is an electric motor which is drivably engaged with the abrasive head 5. The drive unit 6 is operable by a controller 13. The drive unit 6 is operable to rotate the abrasive head 5 during use of the device 1. This aids abrasion of the layer or layers of skin 4 to be removed. Although a drive unit 6 is provided in the present embodiment, it will be understood that the drive unit 6 may be omitted. By omitting the drive unit 6, the arrangement of the head unit 2 is simplified. With such an arrangement the abrasive action is produced by the manual movement of the abrasive head 5 over the user's skin.

The head unit 2 is received by and extends from a body (not shown) of the device 1. Alternatively, it will be understood that the head unit 2 may be spaced from the body of the device 1 and be connected via a flexible tube (not shown) and electric wires (not shown). The electric wires provide power and operating signals to the head unit 2, for example the drive unit 6. The flexible tube (not shown) defines part of the suction path 11.

The suction path 11 extends in the body. The suction path 11 forms a pathway along which air and skin fragments are drawn. The suction path 11 extends from the inlet 12 to an outlet (not shown). Air, together with skin fragments, drawn into the suction path 11 are deposited from the outlet. A collection chamber (not shown) may be disposed at the outlet, and/or a filter to collate the skin fragments and restrict their dispersal into the surrounding atmosphere. The skin fragments may then be disposed of at a later stage.

A vacuum pump 14 is disposed along the suction path 11 to generate a flow of air through the suction path 11. The vacuum pump 14 is conventional and so a detailed description will be omitted herein. The vacuum pump 14 generates a low pressure region on the inlet side of the suction path 11 so that air and skin fragments are drawn into the suction path 11 through the inlet 12.

Figure 2:
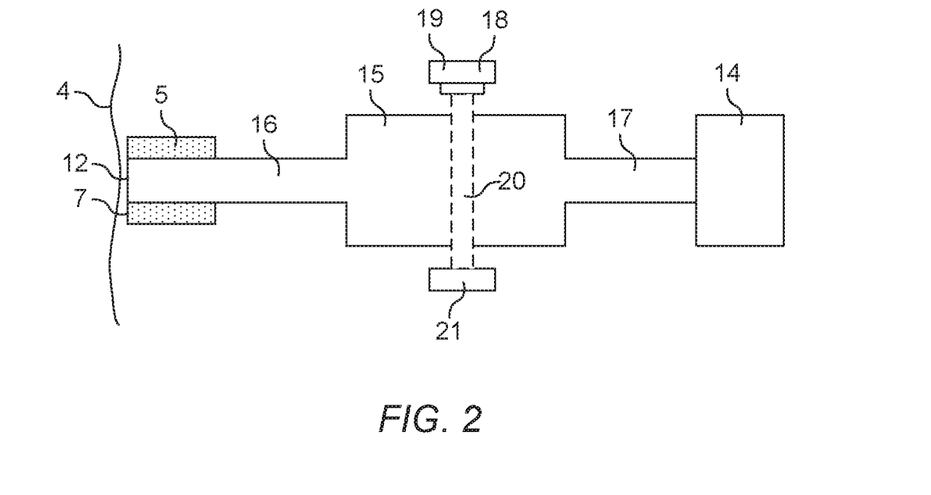
FIG. 2 shows a schematic diagram of part of the microdermabrasion device shown in FIG. 1.

Referring to FIGS. 1 and 2, the detection unit 3 comprises a detection chamber 15. The detection chamber 15 is disposed along the suction path 11. That is, air and skin fragments passing along the suction path 11 pass through the detection chamber 15. A first suction passage 16 is defined between the inlet 12 and the detection chamber 15, and a second suction passage 17 is defined between the detection chamber 15 and the outlet (not shown). The first and second suction passages 16, 17 are formed by tubes. In the present arrangement the detection chamber 15 is disposed along the suction path 11 prior to the vacuum pump 14.

The diameter of the detection chamber 15 is greater than that of the first and second suction passages 16, 17. However, it will be understood that in an alternative arrangement the detection chamber 15 is defined by a section of a tube forming the suction path 11. In such an arrangement the detection chamber 15 does not have different cross-sectional dimensions to the remainder of the suction path 11. In the present arrangement the enlargement of the suction path 11 at the detection chamber 15 provides a reduction in the velocity of the fluid flow through the detection chamber 15 in order to maximise detection accuracy of one or more characteristics of the skin fragments. Alternatively, the detection chamber 15 forms the passage between the inlet 12 and the outlet (not shown).

A detector 18 is disposed in the detection chamber 15. The detector 18 is configured to detect one or more characteristics of abraded skin fragments flowing through the detection chamber 15. The detector 18 comprises a light source 19 configured to generate a focused light beam 20, and a light receiver 21 configured to detect the light beam 20 emitted by the light source 19. The light receiver 21 is a photosensor. It will be understood that alternative detection means may be used to determine one or more characteristics of the abraded skin fragments. The light source 19 and light receiver 21 are disposed outside the detection chamber 15 to prevent skin fragments from accumulating on them. Windows are formed in the detection chamber which correspond to the light source 19 and light receiver 21 of the detector 18. However, it is envisaged that the light source 19 and light receiver 21 may be disposed in the detection chamber 15.

With the present arrangement, the light receiver 21 detects the light beam emitted by the light source 19 during use of the device 1. The detector 18 is configured to detect when a skin fragment passing through the detection chamber 15 impinges on the light beam 20. That is, when a skin fragment passes through the light beam 20, the light emitted by the light source 19 and received by the light receiver 21 is restricted or obscured.

The detector 18 determines when a skin fragment passes through a detection region of the detector 18. The detector 18 is therefore able to determine the number of skin particles passing through the detection chamber 15. This means that it is possible for the detection unit 3 to determine the volume of skin fragments passing along the suction path 11 over time. The controller 13, forming part of the detection unit 3, is configured to compare the determined volume of skin fragments with predetermined threshold values. The predetermined threshold values are stored in a look-up table. The look-up table is stored in a storage module 22. The storage module 22 includes, but is not limited to, volatile memory and non-volatile memory, or other media capable of storing threshold values.

The detection unit 3 further comprises a display 23, acting as a visual feedback module. The display 23 provides an indication of the operating abrasive depth during use of the device 1. Such a display may be configured to indicate the depth, or to indicate when predetermined threshold values are achieved or exceeded. It will be understood that the visual feedback module may have an alternative arrangement, for example an array of lights (not shown). With such an arrangement a first light, for example a green light, may be operated by the controller when the desired abrasive depth is achieved, and a second light, for example a red light, may be operated by the controller when a threshold value for the desired abrasive depth is exceeded. Furthermore, a third light, for example an orange light, may be operated by the controller when another threshold value for the abrasive depth is not achieved. This may indicate when a desired abrasive depth is not being achieved. The threshold values may be a range of depths. The visual display module may form a separate unit.

Although the detection unit 3 comprises a display to act as a visual feedback module, it will be understood that alternative user feedback means may be used. For example, the detection unit 3 may also or alternatively comprise a speaker (not shown), which acts as an audible feedback module, or a vibration unit.

The skin 4 has two primary layers—the epidermis 25 and the dermis 26. The epidermis 25 comprises the outermost layers of the skin. Such layers include the stratum corneum (the outermost layer) 27, the stratum lucidum, stratum granulosum, stratum spinosum, and stratum basale.

During use of the non-particle microdermabrasion device 1, the vacuum pump 14 is operated to generate a flow of air through the suction path 11 such that air is drawn in through the inlet 12 in the abrasive surface 7. The drive unit 6 is operated to rotate the abrasive head 5. The abrasive surface 7 is then brought into contact with the skin 4 of a user. The flow of air through the suction path 11 draws the user's skin against the abrasive surface 7.

When the abrasive surface 7 is moved over a user's skin during use of the device 1, the skin is abraded by the abrasive surface 7 to remove a portion of the skin 4. This produces abraded skin fragments. It will be understood that the depth of abrasion will depend on the pressure exerted by the user on the user's skin or the force applied by the vacuum acting on the skin and generated by the flow of air through the suction path 11.

When the device 1 is operated, the vacuum pump 14 draws a flow of air along the suction path 11. As skin fragments are abraded they are drawn through the inlet 12 of the suction path 11. The skin fragments are then drawn along the suction path 11. As the abraded skin fragments pass along the suction path 11, they pass through the detection chamber 15 of the detection unit 3. The detector 18 is then able to detect the number of abraded skin particles passing through the detector's field over time, and so determine the number of skin fragments passing through the detection chamber 15 over predetermined time periods.

It has been found that the number of skin fragments abraded by the device 1 decreases as the depth of abrasion increases. That is, the number of skin particles abraded in predetermined time periods falls as the abrasive head acts on the deeper skin layers.

The controller 13 compares the number of abraded skin fragments detected by the detector 18 with the stored threshold value or values. When the detection unit 3 determines that the number of abraded skin fragments passing along the suction path 11 is equal to or less than a threshold value, then the detection unit 3 determines that the desired depth of abrasion has been achieved. The detection unit 3 therefore operates the feedback module, in this case the display 23, to indicate to the user that the desired depth of abrasion has been achieved.

If the user continues to abrade the section of skin, the number of abraded skin fragments will fall below another threshold value and the detection unit 3 determines that the desired depth of abrasion has been exceeded. The detection unit 3 therefore operates the feedback module, in this case the display 23, to indicate to the user that the desired depth of abrasion has been exceeded when the value of the number of abraded skin fragments is equal to or less than the another threshold value. It will be understood that in another embodiment the detection unit 3 may only indicate when a single threshold value has been achieved.

With the above arrangement, the user is able to monitor the depth of abrasion being obtained by the device 1 and so adjust operation of the device accordingly. Therefore, the user is able to determine whether a desired depth of abrasion has been achieved, and/or prevent detrimental effects of exceeding a threshold value of depth of abrasion.

The detection unit may be configured to determine the cumulative number of skin fragments determined during a single treatment. The device 1 may also be configured to determine whether the device is in contact with a user's skin, for example through use of a proximity sensor (not shown). In such an arrangement, the detection unit may not be operated.

In the above embodiment the detection unit is configured to determine the operating depth of abrasion based on the number or volume of skin fragments drawn along the suction path and detected by the detector over time. However, it will be understood that, in alternative embodiments, the operating depth of abrasion may be determined by the detection unit determining one or more different characteristics of the skin fragments drawn along the suction path. The arrangement of the alternative embodiments is generally the same as the arrangement of the embodiments described above and so a detailed description will be omitted herein.

In an alternative embodiment, the detection unit is configured to determine the operating depth of abrasion based on the size of skin fragments passing along the suction path 11 during use of the device 1.

With such an arrangement, the detector 18 may be a focused light source and a photosensor, as described above. The detection unit 3 is configured to determine the size of the skin fragments passing along the suction path 11 by determining the length of time the field of the detector 18 is obscured by skin fragments as they pass through the detection chamber. It will be understood that the period of time that the detector 18 is obscured will increase as the size of the abraded skin fragments increase. The length of time that the detector 18 is obscured is dependent on the flow speed along the suction path 11. In the present embodiment, the flow speed is determined to be generally constant, however the detection unit 3 may further comprise a flow speed sensor (not shown) to determine the flow speed along the suction path 11.

It has been found that the size of skin fragments abraded by the device 1 increase as the depth of abrasion increases. That is, the size of skin particles abraded increases as the abrasive head acts on the deeper skin layers.

The controller 13 compares the size of abraded skin fragments detected by the detector 18 with the stored threshold value or values. When the detection unit 3 determines that the size of abraded skin fragments passing along the suction path 11 has is within a threshold range, then the detection unit 3 determines that the desired depth of abrasion has been achieved. The detection unit 3 therefore operates the feedback module, in this case the display 23, to indicate to the user that the desired depth of abrasion has been achieved.

If the user continues to abrade the section of skin, the size of abraded skin fragments will increase to be equal to or greater than another threshold value and the detection unit 3 then determines that the desired depth of abrasion has been exceeded. The detection unit 3 therefore operates the feedback module, in this case the display 23, to indicate to the user that the desired depth of abrasion has been exceeded. It will be understood that in another embodiment the detection unit 3 may only indicate when a single threshold value has been achieved In an alternative arrangement, the detection unit 3 is configured to determine the operating depth of abrasion based on the temperature of skin fragments passing along the suction path 11 during use.

The temperature of the skin fragments may be determined by the detection unit 3 determining infrared radiation. For example, an infrared sensor may be used.

Experiments have found that the temperature of skin fragments abraded by the device 1 increases as the depth of abrasion increases. That is, the temperature of skin particles abraded increases as the abrasive head acts on the deeper skin layers.

With such an arrangement, the controller 13 compares the temperature of abraded skin fragments detected by the detector 18 with the stored threshold value or values. When the detection unit 3 determines that the temperature of abraded skin fragments passing along the suction path 11 is equal to or greater than a threshold value, then the detection unit 3 determines that the desired depth of abrasion has been achieved. The detection unit 3 therefore operates the feedback module, in this case the display 23, to indicate to the user that the desired depth of abrasion has been achieved.

If the user continues to abrade the section of skin, the temperature of abraded skin fragments will increase to be equal to or greater than another threshold value. The detection unit 3 then determines that the desired depth of abrasion has been exceeded. The detection unit 3 therefore operates the feedback module, in this case the display 23, to indicate to the user that the desired depth of abrasion has been exceeded. It will be understood that in another embodiment the detection unit 3 may indicate when only a single threshold value or multiple threshold values has been achieved.

Alternatively, may be based on the temperature difference compared to the base temperature of the fragments detected upon start of operation of the device. With such an arrangement the threshold values are based on temperature difference.

In an alternative arrangement, the detection unit 3 is configured to determine the operating depth of abrasion based on the weight of the skin fragments passing along the suction path during use. In one embodiment the detection chamber 15 is a cylindrical centrifugal chamber, and the weight of the skin fragments is determined through the use of a centrifuge detection configuration.

Experiments have found that the weight of skin fragments abraded by the device 1 increases as the depth of abrasion increases. It has been found that an increase in the weight of the skin fragments detected indicates an increase in the cell content of the skin fragments. Therefore, it has been found that the weight of skin particles abraded increases as the abrasive head acts on the deeper skin layers.

With such an arrangement, the controller 13 compares the weight of abraded skin fragments detected by the detector 18 with the stored threshold value or values. When the detection unit 3 determines that the weight of abraded skin fragments passing along the suction path 11 is equal to or greater than a threshold value, then the detection unit 3 determines that the desired depth of abrasion has been achieved. The detection unit 3 therefore operates the feedback module, in this case the display 23, to indicate to the user that the desired depth of abrasion has been achieved.

If the user continues to abrade the section of skin, the weight of abraded skin fragments will increase to be equal to or greater than another threshold value. The detection unit 3 then determines that the desired depth of abrasion has been exceeded. The detection unit 3 therefore operates the feedback module, in this case the display 23, to indicate to the user that the desired depth of abrasion has been exceeded. It will be understood that in another embodiment the detection unit 3 may indicate when only a single threshold value or multiple threshold values has been achieved.

In an alternative arrangement, the detection unit 3 is configured to determine the operating depth of abrasion based on the water content of the skin fragments passing along the suction path during use. With such an arrangement, the detector is configured to detect a predetermined absorption spectrum, or a specific wavelength, that is only or primarily absorbed by water. In one embodiment the detector is configured to detect a wavelength equal to or greater than 1000 nm.

Experiments have found that the water content of skin fragments abraded by the device 1 increases as the depth of abrasion increases. That is, it has been found that the water content of skin particles abraded increases as the abrasive head acts on the deeper skin layers.

With such an arrangement, the controller 13 compares the water content of abraded skin fragments detected by the detector 18 with the stored threshold value or values. When the detection unit 3 determines that the water content of abraded skin fragments passing along the suction path 11 is equal to or greater than a threshold value, then the detection unit 3 determines that the desired depth of abrasion has been achieved. The detection unit 3 therefore operates the feedback module, in this case the display 23, to indicate to the user that the desired depth of abrasion has been achieved.

If the user continues to abrade the section of skin, the water content of abraded skin fragments will increase to be equal to or greater than another threshold value. The detection unit 3 then determines that the desired depth of abrasion has been exceeded. The detection unit 3 therefore operates the feedback module, in this case the display 23, to indicate to the user that the desired depth of abrasion has been exceeded. It will be understood that in another embodiment the detection unit 3 may indicate when only a single threshold value or multiple threshold values has been achieved.

In an alternative arrangement, the detection unit is configured to determine the operating depth of abrasion based on the scattering co-efficient of the skin fragments passing along the suction path during use. In one such embodiment, the light source and light receiver of the detector are offset from each other. Therefore, the detector is configured to detect the scattering contribution of the skin fragments, rather the transmission or reflection thereof.

Experiments have found that the scattering co-efficient of skin fragments abraded by the device 1 decreases as the depth of abrasion increases. It has been found that a decrease in the scattering co-efficient of the skin fragments detected indicates less dry skin fragments. Therefore, it has been found that the scattering co-efficient of skin particles abraded decreases as the abrasive head acts on the deeper skin layers.

With such an arrangement, the controller 13 compares the scattering co-efficient of abraded skin fragments detected by the detector 18 with the stored threshold value or values. When the detection unit 3 determines that the scattering co-efficient of abraded skin fragments passing along the suction path 11 is equal to or less than a threshold value, then the detection unit 3 determines that the desired depth of abrasion has been achieved. The detection unit 3 therefore operates the feedback module, in this case the display 23, to indicate to the user that the desired depth of abrasion has been achieved.

If the user continues to abrade the section of skin, the scattering co-efficient of abraded skin fragments will decrease to be equal to or less than another threshold value. The detection unit 3 then determines that the desired depth of abrasion has been exceeded. The detection unit 3 therefore operates the feedback module, in this case the display 23, to indicate to the user that the desired depth of abrasion has been exceeded. It will be understood that in another embodiment the detection unit 3 may indicate when only a single threshold value or multiple threshold values has been achieved.

In an alternative arrangement, the detection unit is configured to determine the operating depth of abrasion based on detecting the absorption profile of the skin fragments or the absorption of a single wavelength of the skin fragments passing along the suction path during use.

Experiments have found that detecting the absorption profile of the skin fragments or the absorption of a single wavelength of the skin fragments can provide an indication of skin content concentrations of water (infra-red wavelength), blood or melanin (blue wavelength). In one embodiment, the detector is configured to detect the quantity of melanin in the skin fragments. With such an arrangement, the detector is configured to detect wavelengths in the range of 350 to 450 nm. In another embodiment, the detector is configured to detect the quantity of sebum in the skin fragments. With such an arrangement, the detector is configured to detect wavelengths equal to or greater than 1000 nm, and in particular wavelengths of 920 nm, 1210 nm and/or 1720 nm.

With such an arrangement, the controller 13 compares the absorption profile of the skin fragments or the absorption of a single wavelength of the skin fragments detected by the detector 18 with the stored absorption profile or absorption of a single wavelength. When the detection unit 3 determines that the absorption profile of the abraded skin fragments or the absorption of a single wavelength of the abraded skin fragments passing along the suction path 11 corresponds to a stored absorption profile or the absorption of a single wavelength, then the detection unit 3 determines that the desired depth of abrasion has been achieved. The detection unit 3 therefore operates the feedback module, in this case the display 23, to indicate to the user that the desired depth of abrasion has been achieved.

If the user continues to abrade the section of skin, the absorption profile of the abraded skin fragments or the absorption of a single wavelength of the skin fragments of abraded skin fragments will correspond to another stored absorption profile or absorption of a single wavelength. The detection unit 3 then determines that the desired depth of abrasion has been exceeded. The detection unit 3 therefore operates the feedback module, in this case the display 23, to indicate to the user that the desired depth of abrasion has been exceeded. It will be understood that in another embodiment the detection unit 3 may indicate when the absorption profile or the absorption of a single wavelength corresponds to a single or multiple absorption profiles of the skin fragments or the absorption of a single wavelength of the skin fragments.

Although in the above embodiment one detector is used to determine the operating depth of abrasion, it will be understood that in alternative embodiments two or more detectors are used to determine one or more characteristics of the skin fragments in order to determine the operating depth of abrasion. The arrangement of the alternative embodiments is generally the same as the arrangement of the embodiments described above and so a detailed description will be omitted herein.

Figure 3:
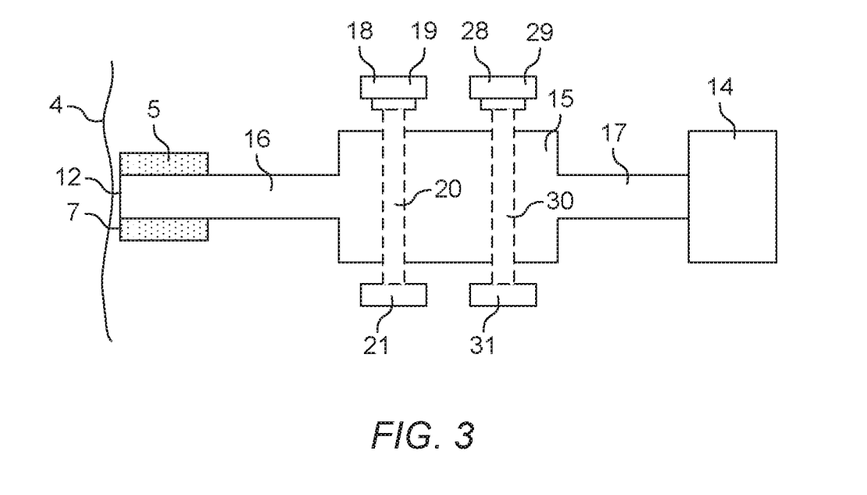
FIG. 3 shows a schematic diagram of part of another embodiment of the microdermabrasion device shown in FIG. 1.

In such an embodiment, first and second detectors 18, 28 are used. Such an embodiment is shown in FIG. 3. With such an arrangement, the first detector 18 is configured to detect one or more characteristics of abraded skin fragments flowing through the detection chamber 15. The first detector 18 comprises a first light source 19 configured to generate a first focused light beam 20, and a first light receiver 21 configured to detect the first light beam 20 emitted by the first light source 19. It will be understood that alternative detection means may be used to determine one or more characteristics of the abraded skin fragments. The second detector 28 comprises a second light source 29 configured to generate a second focused light beam 30, and a second light receiver 31 configured to detect the second light beam 30 emitted by the second light source 29. It will be understood that alternative detection means may be used to determine one or more characteristics of the abraded skin fragments.

In the present arrangement, the first and second detectors 18, 28 are configured to detect different characteristics of the abraded skin fragments. For example, the first detector 18 may be configured to detect the size of the skin fragments, and the second detector 28 may be configured to detect the number of skin fragments. However, it will be understood that the first and second detectors 18, 28 may be configured to detect the same characteristic of the abraded skin fragments.

By having two detectors it is possible to maximise the accuracy of the operating depth of abrasion determined.

Although in the above described embodiments the microdermabrasion device is of the non-particle microdermabrasion type, the device may be a particle microdermabrasion device.

With such an arrangement, a high pressure stream of particles, such as aluminium oxide, magnesium oxide, sodium chloride, or sodium bicarbonate particles are directed towards the skin to abrade the skin and remove skin fragments from the upper layer or layers of skin (not shown). A vacuum is also produced to remove the abrasive particles and exfoliated skin fragments from the area of the skin (not shown). With a particle microdermabrasion device the arrangement of the suction path and the detection unit will be generally the same. However, particles will pass along the suction path together with the skin fragments.

However, in an arrangement using particles as the abrasive medium, the detection unit is able to differentiate between the particles and the skin fragments based on one or more of their characteristics, such as their absorption profile, their size, or their weight. For example, the particles may be configured to have a different characteristic range, such as a different size range, to the skin fragments abraded so that the detection unit is able to distinguish between the particles and skin fragments and so provide feedback on the characteristics of the skin fragments detected only.

Alternatively, or in addition, to the forgoing, the detection unit may be configured to determine one or more characteristics based on the combined profile of the skin fragments and abrasive particles, for example total number of skin fragments and abrasive particles detected passing through the detection chamber.

It will also be understood that the detection unit may be able to detect characteristics of the skin fragments independent of the abrasive particles, because such characteristics depend on the skin fragments only and not the abrasive material. For example, the temperature and/or water content determined in the flow path is dependent on the characteristics of the skin fragments only. Therefore, such an arrangement described above for non-particle operation may be easily used with particle operation.

The head unit described in the above embodiments may be a separate head unit that is attachable to the remainder of the device. The head unit may be removed to clean the head unit or to replace the head unit or components of the head unit after they have become worn.

It will be understood that the abrasive head described in the above embodiments may be a separate abrasive head that is attachable to the head unit. The abrasive head may be removed to clean the abrasive head or to replace the abrasive head after they have become worn.

It will be understood that it is not possible to use the above arrangements with a particle microdermabrasion device. With particle abrasion a high pressure stream of particles, such as aluminium oxide, magnesium oxide, sodium chloride, or sodium bicarbonate particles are directed towards the skin to abrade the skin and remove skin fragments from the upper layer or layers of skin. The abrasive particles will then flow along the suction path along with the abraded skin fragments. Therefore, the particles will also be detected by a detection unit and it will not be possible to determine the characteristics of the skin fragments separate from the characteristics of the abrasive particles. This means that is would not be possible to determine the depth of abrasion.

It will be understood that the above-described devices and method of determining the depth of abrasion of a microdermabrasion device may relate to a cosmetic treatment by administration of the device. That is, the described devices may be a cosmetic device, and the described methods may be a cosmetic treatment.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A microdermabrasion device comprising:
    a suction path along which skin fragments removed by the device are drawn, and
    a detection unit, comprising a focused light source configured to generate a focused light beam and a photosensor
    wherein the detection unit is configured to determine one or more characteristics of skin fragments drawn along the suction path,
    wherein the detection unit is further configured to determine the depth of abrasion performed by the device based on the one or more determined characteristics of skin fragments drawn along the suction path, and
    wherein the detection unit further comprises a detector disposed on the suction path to detect one or more characteristics of skin fragments drawn along the suction path.

2. A microdermabrasion device according to claim 1, wherein the detection unit comprises at least two detectors and the detection unit further comprises a second detector disposed on the suction path to detect one or more characteristics of skin fragments drawn along the suction path.

3. A microdermabrasion device according to claim 2, wherein the first and second detectors are each configured to detect different characteristics of skin fragments drawn along the suction path.

4. A microdermabrasion device according to claim 1, wherein the detection unit further comprises a feedback module configured to provide feedback to the user based on the operating depth of abrasion determined by the detection unit.

5. A microdermabrasion device according to claim 4, wherein the feedback module is configured to provide a visual, mechanical and/or audible indication.

6. A microdermabrasion device according to claim 1, wherein the detector comprises a photosensor.

7. A microdermabrasion device according to claim 1, wherein the detection unit is configured to determine the number of skin fragments drawn along the suction path and/or the size of skin fragments drawn along the suction path.

8. A microdermabrasion device according to claim 1, wherein the detection unit is configured to determine the temperature of skin fragments drawn along the suction path and/or the weight of skin fragments drawn along the suction path.

9. A microdermabrasion device according to claim 1, wherein the detection unit is configured to determine the water content of skin fragments drawn along the suction path and/or the scattering co-efficient of skin fragments drawn along the suction path.

10. A microdermabrasion device according to claim 1, wherein the detection unit is configured to determine the absorption profile of skin fragments drawn along the suction path and/or the absorption of a single wavelength of skin fragments drawn along the suction path.

11. A microdermabrasion device according to claim 1, wherein the device is a non-particle microdermabrasion device.

12. A method of determining the depth of abrasion of a microdermabrasion device characterized in that the method comprises the steps of:
    determining one or more characteristics of skin fragments drawn along a suction path of the device, and
    determining the depth of abrasion performed by the device based on the one or more characteristics of skin fragments drawn along the suction path, and
    providing via a display, configured as a visual feedback module, a visual indication of one of, the operating abrasive depth via visual feedback, based on the determined depth of abrasion, and an indication when predetermined threshold values of the depth of abrasion are achieved or exceeded.

13. A method according to claim 12, further comprising determining one or more of the volume of skin fragments drawn along the suction path, the size of skin fragments drawn along the suction path, the temperature of skin fragments drawn along the suction path, the weight of skin fragments drawn along the suction path, the water content of skin fragments drawn along the suction path, the scattering co-efficient of skin fragments drawn along the suction path, the absorption profile of skin fragments drawn along the suction path, and/or the absorption or a single wavelength of the skin fragments drawn along the suction path.

14. A method according to claim 12, further comprising providing visual or audible feedback based on the determined depth of abrasion.

15. A method of determining the depth of abrasion of a microdermabrasion device characterized in that the method comprises the steps of:
- determining one or more characteristics of skin fragments drawn along a suction path of the device, and
- determining the depth of abrasion performed by the device based on the one or more characteristics of skin fragments drawn along the suction path, and
- providing via an audio feedback module, an audible indication of one of:
- the operating abrasive depth via an audio feedback, based on the determined depth of abrasion, and
- an indication when predetermined threshold values of the depth of abrasion are achieved or exceeded.

* * * * *